United States Patent
Lemchen (12)

(10) Patent No.: US 7,878,806 B2
(45) Date of Patent: Feb. 1, 2011

(54) APPARATUS AND METHOD FOR INDIRECT ORTHODONTIC BONDING OF BRACKETS AND/OR TUBES

(76) Inventor: Marc S. Lemchen, 553 Park Ave., New York, NY (US) 10021

( * ) Notice: Subject to any disclaimer, the term of this patent is extended or adjusted under 35 U.S.C. 154(b) by 268 days.

(21) Appl. No.: 12/125,743

(22) Filed: May 22, 2008

(65) Prior Publication Data

US 2008/0293004 A1    Nov. 27, 2008

Related U.S. Application Data

(60) Provisional application No. 60/940,058, filed on May 24, 2007.

(51) Int. Cl.
*A61C 3/00*    (2006.01)
(52) U.S. Cl. .............................. 433/24; 433/3
(58) Field of Classification Search ............... 433/3, 433/9, 24
See application file for complete search history.

(56) References Cited

U.S. PATENT DOCUMENTS 4,551,096 A * 11/1985 Dellinger .................. 433/24
5,863,198 A * 1/1999 Doyle ............................ 433/3
6,123,544 A * 9/2000 Cleary .......................... 433/24

OTHER PUBLICATIONS

JCO Interviews Dr. Homer W. Phillips on Bonding Part 1, vol. 14: No. 06, p. 391-411, 1980.*

* cited by examiner

*Primary Examiner*—Cris L Rodriguez
*Assistant Examiner*—Heidi M Eide
(74) *Attorney, Agent, or Firm*—Marcus C. Dawes; Daniel L. Dawes

(57) ABSTRACT

The illustrated embodiment of the invention is an apparatus for use in bonding a plurality of brackets and/or tubes to a specific patient's teeth which includes a resilient orthodontic indirect bonding tray having at least one lingual surface. The plurality of brackets and/or tubes is selectively arranged and configured in the tray for bonding to the specific patient's teeth. At least one standoff is disposed in the tray to urge the lingual surface of the tray away from the teeth while the lingual surface is passing over the teeth and prior to the tray assuming an intended final position.

4 Claims, 3 Drawing Sheets

APPARATUS AND METHOD FOR INDIRECT ORTHODONTIC BONDING OF BRACKETS AND/OR TUBES

RELATED APPLICATIONS

The present application is related to U.S. Provisional Patent Application Ser. No. 60/940,058, filed on May 24, 2007, which is incorporated herein by reference and to which priority is claimed pursuant to 35 USC 119.

BACKGROUND OF THE INVENTION

1. Field of the Invention

The invention relates to the field of orthodontic devices, and in particular to an indirect bonding tray and method of using the same.

2. Description of the Prior Art

Indirect bonding is comprised of setting the brackets and/or tubes 10 for an orthodontic case on a model of the teeth 14 in a desired position on the teeth 14, which model is virtual or real (i.e. made of plaster, plastic, CAD/CAM prototyped). The brackets and/or tubes 10 are appropriately arranged in a tray 12, which is typically comprised of a soft, resilient mold in which the brackets or tubes 10 are temporarily embedded. The tray is then positioned into the patient's mouth and the brackets or tubes 10 affixed to the patient's teeth 14 with adhesive that has previously been disposed onto the brackets or tubes 10 prior to placement. As diagrammatically shown in side cross sectional view of FIG. 1, brackets 10 may be set virtually using a prediction of the desired result and then transferred virtually or in reality back to the model of the patient's teeth 14 in the arrangement and configuration in which they will be set in reality. The tray 12 is removed, and the brackets or tubes 10 stay will stay affixed to the patient's teeth 14 by virtue of the bonding achieved through the adhesive.

When the trays 12 are seated in the patient's mouth, the seating path often "wipes" at least part of the adhesive off the bracket and/or tube 10, and further does nothing to help impress the adhesive into the wire mesh backing (not shown) used on most brackets 10 nor hold the adhesive in contact with the mechanical/chemical bonding surface of a ceramic bracket 10. Most bracket bonding failures are due to poor bonding to the bracket 10, and not due to the tooth 14, so the more intimate the contact between the bracket 10 and adhesive layer 24, the better the fixation of the brackets and/or tubes 10 are to the teeth 14.

BRIEF SUMMARY OF THE INVENTION

The illustrated embodiment of the invention is an apparatus for use in bonding a plurality of brackets and/or tubes to a specific patient's teeth comprising a resilient orthodontic indirect bonding tray having at least one lingual surface. The plurality of brackets and/or tubes is selectively arranged and configured in the tray for bonding to the specific patient's teeth. At least one standoff is disposed in the tray to urge the lingual surface of the tray away from the teeth while the lingual surface is passing over the teeth and prior to the tray assuming an intended final position.

An adhesive layer is selectively disposed on a bonding surface on each of the plurality of brackets and/or tubes. The at least one standoff urges the buccal and/or lingual surface of the tray away from the teeth to allow the adhesive layer on the bonding surfaces to clear the teeth until the standoff reaches its intended final position relative to the tooth where the tray is allowed to close down on the teeth bringing the adhesive layer on the bonding surfaces of the plurality of brackets and/or tubes into contact with the teeth.

The at least one standoff holds the adhesive layer on the bonding surfaces off the teeth until the tray is fully seated in the intended final position, so that substantially no adhesive is wiped off the bonding surfaces. It is understood by those having ordinary skill in orthodontics that while some adhesive may be wiped off, that "substantially no adhesive" means that a sufficient amount remains on the bonding surfaces to reliably bond the brackets and/or tubes to the teeth in the described setting.

When the at least one standoff is fully seated in the intended final position, the tray resiliently closes down on the teeth to force the adhesive layer into a bonding interface between each of the teeth and the corresponding ones of the plurality of brackets and/or tubes.

When the at least one standoff is fully seated in the intended final position, the tray resiliently closes down on the teeth to force the adhesive layer into intimate contact the bonding surfaces of the plurality of brackets and/or tubes with a corresponding surface of each of teeth.

In another embodiment the apparatus further comprising a plurality of standoffs arranged and configured in the tray to be disposed into an interproximal area between adjacent teeth when the tray is fully seated in the intended final position.

The at least one standoff comprises a bump, ramp, post, projection or clasp.

The at least one standoff comprises a detent mechanism for temporarily fixing or locking the tray into a bonding location with respect to the teeth.

The illustrated embodiment of the invention is also a method for bonding a plurality of brackets and/or tubes to a specific patient's teeth comprising the steps of providing a resilient orthodontic indirect bonding tray having at least one lingual surface, arranging and configuring the plurality of brackets and/or tubes in the tray for bonding to the specific patient's teeth, where each of the plurality of brackets and/or tubes having a corresponding bonding surface, applying an adhesive to the bonding surfaces, moving the tray into the patient's mouth along a seating path, and urging the lingual surface of the tray away from the teeth while the tray is moving along the seating path.

The step of urging the buccal lingual surface of the tray away from the teeth while the tray is moving along the seating path comprises the step urging the lingual surface of the tray away from the teeth by interposing at least one standoff between the teeth and the tray until an intended final position is obtained.

The illustrated embodiment of the method further comprises the step of closing the lingual surface of the tray down on the teeth to bring the adhesive on the bonding surfaces of the plurality of brackets and/or tubes into contact with the teeth.

The illustrated embodiment of the method further comprises avoiding wiping off any substantial amount of adhesive from the bonding surfaces while moving the tray. Again, it is understood by those having ordinary skill in orthodontics that while some adhesive may be wiped off, that "avoiding wiping off any substantial amount of adhesive" means that a sufficient amount remains on the bonding surfaces to reliably bond the brackets and/or tubes to the teeth in the described setting.

The illustrated embodiment of the method further comprises the step of resiliently closing the tray down on the teeth to force the adhesive layer into a bonding interface between each of the teeth and the corresponding ones of the plurality of brackets and/or tubes, when the at least one standoff is fully sealed in the intended final position.

The illustrated embodiment of the method further comprises the step of resiliently closing the tray down on the teeth to force the adhesive layer into intimate contact the bonding surfaces of the plurality of brackets and/or tubes with a corresponding surface of each of teeth, when the at least one standoff is fully seated in the intended final position.

The illustrated embodiment of the method further comprises the step of arranging and configuring a plurality of standoffs in the tray to be disposed into an interproximal area between adjacent teeth when the tray is fully seated in the intended final position.

The illustrated embodiment of the method further comprises the step of temporarily fixing or locking the tray into a bonding location with respect to the teeth by using the at least one standoff as a detent mechanism.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 1:
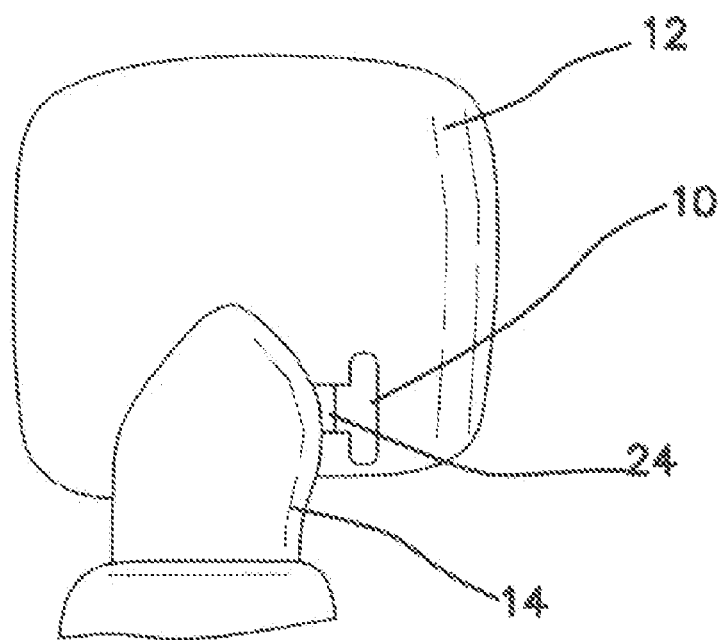
FIG. 1 is a cross sectional depiction of an indirect orthodontic bonding tray of the prior art.
Figure 2:
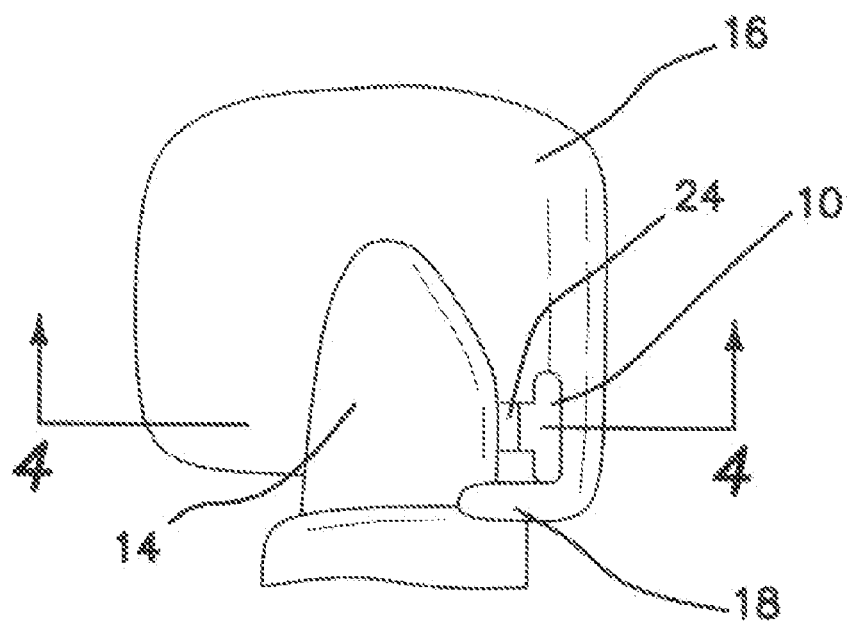
FIG. 2 is a cross sectional depletion of an indirect orthodontic bonding tray according to the illustrated embodiment of the invention showing the bracket in contact with the tooth.

As diagrammatically shown in the side cross sectional view of FIG. 2 improved tray 16 of the illustrated embodiment has a design feature to put "bumps", "ramps" or "clasps" in the tray 16, that act as standoffs 18 while passing over the teeth 14 and prior to locking into their intended final position. Tray 16 is made of a resilient material such as a soft resilient polymer or plastic and includes conventional means for mounting brackets or tubes 10 into position in the tray to match the tooth arrangement of a patient. It must be understood that the means for mounting brackets or tubes 10 into an arrangement in tray 16 is secondary to the implementation of the illustrated embodiment of the invention and any means for such mounting now known or later devised may be equivalents employed.

Figure 4:
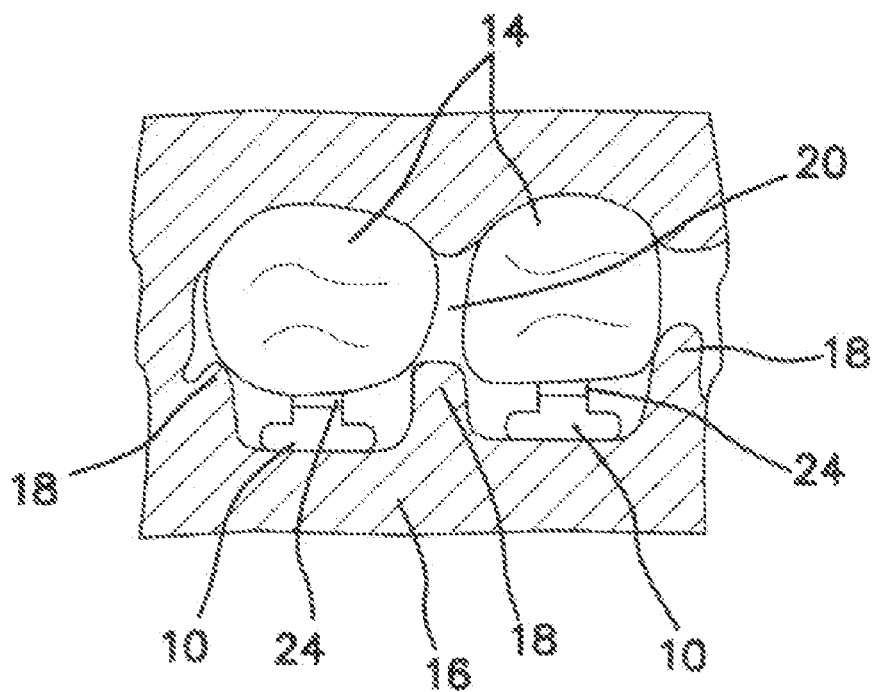
FIG. 4 is an orthogonal cross sectional view as seen through lines 4-4 of FIG. 2 of an indirect orthodontic bonding tray according to the illustrated embodiment of the invention showing the bracket in contact with the tooth.

Standoffs 18 are "bumps", "ramps" or "clasps" which can also be mounted inside tray 16 in an arrangement configured relative to the brackets or tubes 10 and hence relative to the teeth 14 to which such brackets or tubes 10 will be affixed. Standoffs 18 may include molded contours on the inner buccal and/or lingual surfaces of tray 16 which are custom molded to uniquely fit the patient's mouth. However, in the preferred embodiment, standoffs 18 are selectively placed posts, ramps or projections. When not aligned with the teeth in their final position, standoffs 18 open up or splay the flexible tray 16 away from the teeth 14 to allow the adhesive 24 on the back of the imbedded orthodontic brackets 10 to clear the tooth surface, until the standoff 18 reaches its correct position, which is usually past the point 22 of highest curvature of the tooth 14 or interproximal area 20 shown in the top cross sectional view of FIG. 4 and in the top plan view of FIG. 5. In other words, a plurality of standoffs 18 are provided on each lingual side of tray 16 and have a pattern such that only the final position will be one that allows all the standoffs 18 to be properly aligned with a corresponding interproximal area 20. Only then can tray 16 resiliently snug into or tighten down on the teeth 14. In all other positions of tray 16 as it is being moved into the mouth, at least one standoff will be in a non-mating position with the teeth 14 and will keep the entire lingual side of tray 16 away from the teeth 14.

Figure 3:
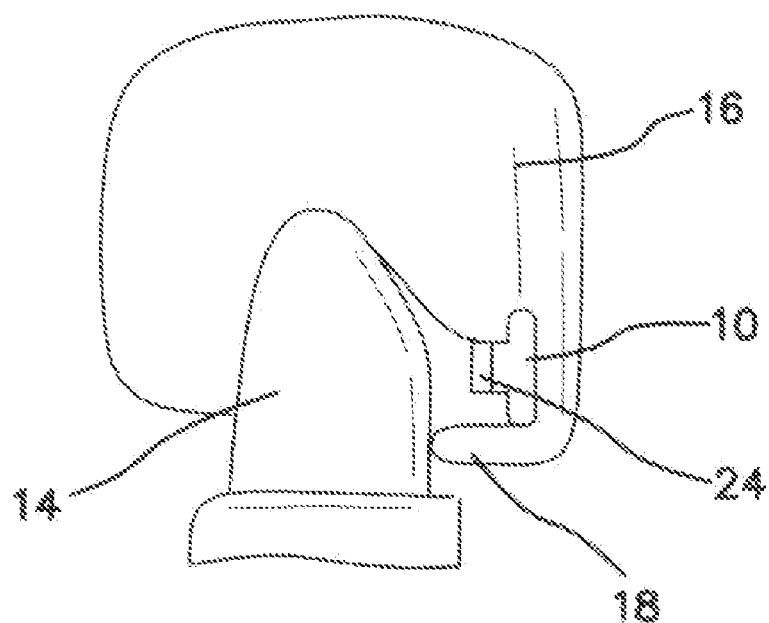
FIG. 3 is a cross sectional depiction of an indirect orthodontic bonding tray according to the illustrated embodiment of the invention showing the bracket held out of contact from the tooth.

Thus, standoffs 18 allow the tray 16 to close down or snug into teeth 14. The standoffs function essentially as a detent mechanism for temporarily fixing or locking tray 16 into a bonding location with respect to the teeth 14. As shown in the partially seated tray 16 in side cross sectional view of FIG. 3, the bracket 10 and adhesive 24 are temporarily held away from tooth 24 by standoff 18, but when standoff 18 reaches an interproximal area 20 between adjacent teeth if moves into the interproximal area 20 allowing the natural resiliency of tray 16 to force adhesive 24 on bracket 10 onto the tooth surface and also pressing the adhesive into the mesh, which may be provided on the mounting surface of the bracket 10. The imbedded brackets 10 move closer to the tooth surface bringing the bonding adhesive 24 into contact with the tooth surface, forcing the adhesive into the mesh or into intimate contact with the mechanical/chemical bonding surface of the bracket 10.

The purpose is to allow the seating of the tray 16 into the teeth 14 without wiping off the adhesive 24 as the tray 16 is placed and secondly to force the adhesive into the bonding interface between the tooth 14 and bracket 10.

Figure 5:
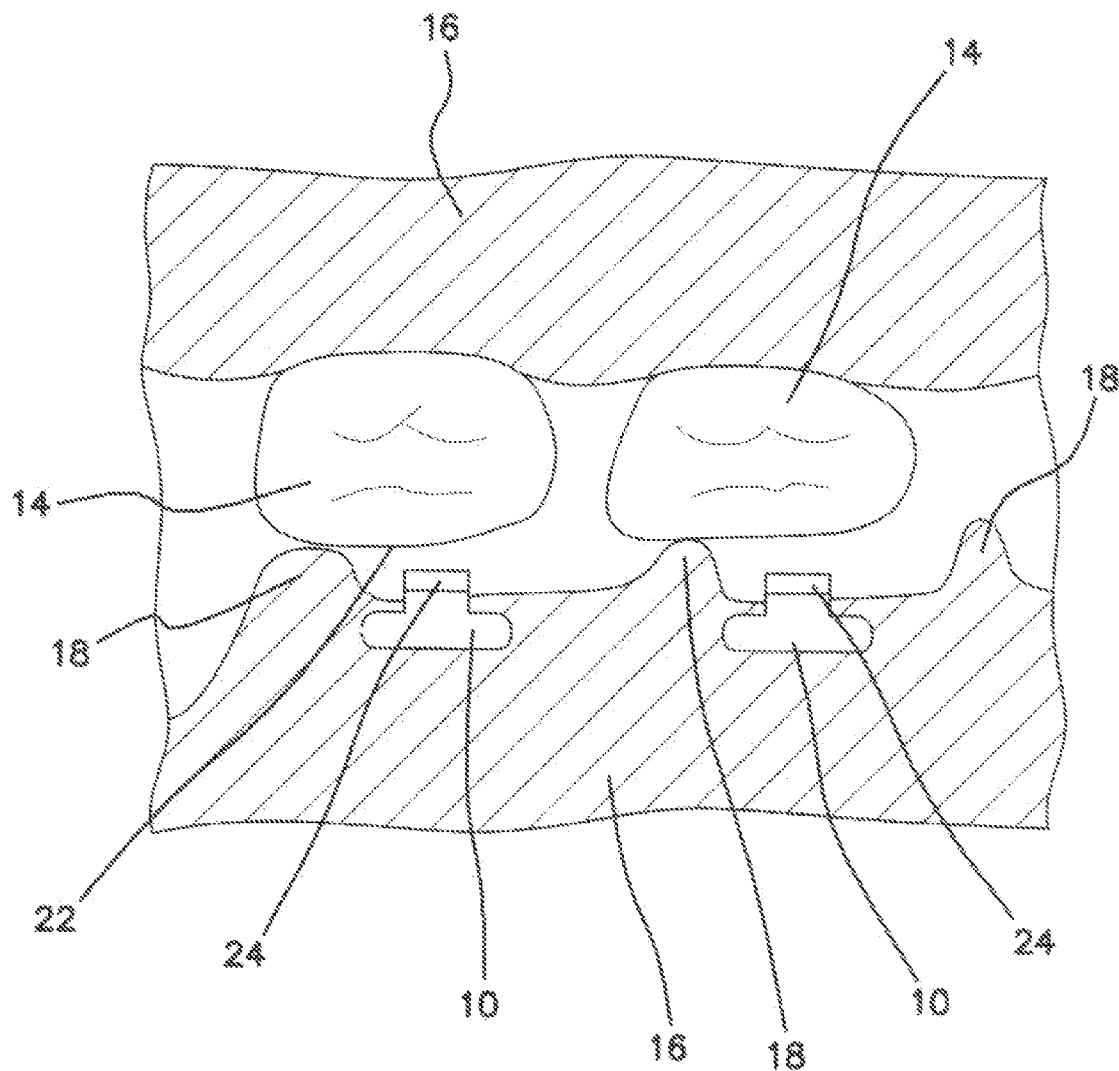
FIG. 5 is a plan view of an indirect orthodontic bonding tray according to the illustrated embodiment of the invention showing the bracket held out of contact with the tooth.

As shown in the top cross sectional view of FIG. 5 the tray 16 flexes out when seating on teeth 14 and snaps closed when fully seated, thereby pushing adhesive 24 into the bonding surface of the bracket where the adhesive 24 mechanically or chemically interlocks on the back of bracket or tube 10, while avoiding any wiping action which might remove some or even most of the adhesive 24 from the bonding surface of the tooth.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination Insubstantial changes from the claimed subject matter as viewed by a person with ordinary skill in the art, now known or later devised, are expressly contemplated as being equivalency within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. A method for bonding a plurality of brackets and/or tubes to a specific patient's teeth comprising:
   providing a resilient orthodontic indirect bonding tray;
   arranging and configuring the plurality of brackets and/or tubes in the tray for bonding to the specific patient's teeth, each of the plurality of brackets and/or tubes having a corresponding bonding surface;
   applying an adhesive to the bonding surfaces of the brackets and/or tubes;
   moving the tray carrying the brackets and/or tubes with the applied adhesive into the patient's mouth along a seating path;
   urging the resilient tray away from the teeth while the tray is moving along the seating path using at least one standoff integrally extending from the tray and contacting the teeth in an interference misalignment between the at least one standoff and the teeth to keep the brackets and/or tubes with the applied adhesive out of contact with the teeth; and
   contracting the resilient tray onto the teeth by interposing the at least one standoff between the teeth in an alignment fit when the tray reaches an intended final position to bring the bonding surfaces of the brackets and/or tubes with the applied adhesive into contact with the teeth for the first time.

2. The method of claim 1 further comprises avoiding wiping off any substantial amount of adhesive from the bonding surfaces while moving the tray.

3. The method of claim 1 further comprising arranging and configuring a plurality of standoffs in the tray to be disposed into an interproximal between adjacent teeth when the tray is fully seated in the intended final position.

4. The method of claim 1 further comprising temporarily fixing or locking the tray into a bonding location with respect to the teeth by using the at least one standoff as a detent mechanism.

* * * * *